(12) United States Patent
Cooper

(10) Patent No.: US 6,252,663 B1
(45) Date of Patent: Jun. 26, 2001

(54) SCANNING AND PRINTING SYSTEMS WITH COLOR DISCRIMINATION

(75) Inventor: Ted J. Cooper, Sunnyvale, CA (US)

(73) Assignees: Sony Corporation, Tokyo (JP); Sony Electronics, Inc., Park Ridge, NJ (US)

( * ) Notice: Subject to any disclaimer, the term of this patent is extended or adjusted under 35 U.S.C. 154(b) by 0 days.

(21) Appl. No.: 09/290,148

(22) Filed: Apr. 12, 1999

(51) Int. Cl.[7] .................................................. G01N 21/25
(52) U.S. Cl. ............................................ 356/416; 356/419
(58) Field of Search .................................... 356/416, 402, 356/400, 399, 401, 410, 326, 328, 330–334, 73; 250/226, 208, 209, 229, 578, 237, 239

(56) References Cited

U.S. PATENT DOCUMENTS

| | | | |
|---|---|---|---|
| 3,880,523 | * 4/1975 | Thomas | 356/79 |
| 3,973,118 | 8/1976 | LaMontagne | 250/226 |
| 4,079,388 | 3/1978 | Takahama et al. | 354/31 |
| 4,308,456 | 12/1981 | Van Der Gaag et al. | 250/226 |
| 4,653,925 | 3/1987 | Thornton, Jr. | 356/419 |
| 4,896,965 | 1/1990 | Goff et al. | 356/417 |
| 5,272,518 | 12/1993 | Vincent | 356/405 |
| 5,500,709 | 3/1996 | Kazami et al. | 354/416 |
| 5,568,267 | 10/1996 | Sunamori et al. | 356/307 |
| 5,654,809 | 8/1997 | Beeman et al. | 358/504 |
| 5,684,582 | * 11/1997 | Eastman et al. | 356/328 |
| 5,710,948 | 1/1998 | Takagi | 396/50 |
| 5,799,216 | 8/1998 | Teremy et al. | 396/225 |

* cited by examiner

Primary Examiner—Frank G. Font
Assistant Examiner—Michael P. Stafira
(74) Attorney, Agent, or Firm—Mikio Ishimaru

(57) ABSTRACT

A document processing system is provided having an optical sensor system for taking an original color image and compensating for process related variations in the scanning or printing process to provide a scanned or printed image having the color appearance of the original image. The document processing system is provided with the optical sensor system responsive to the scanned document intensity spectrum through a bandpass filter or diffraction grating to provide color compensation for different color variations in the paper, the scanner light source, or the printer color toners or ink.

18 Claims, 2 Drawing Sheets

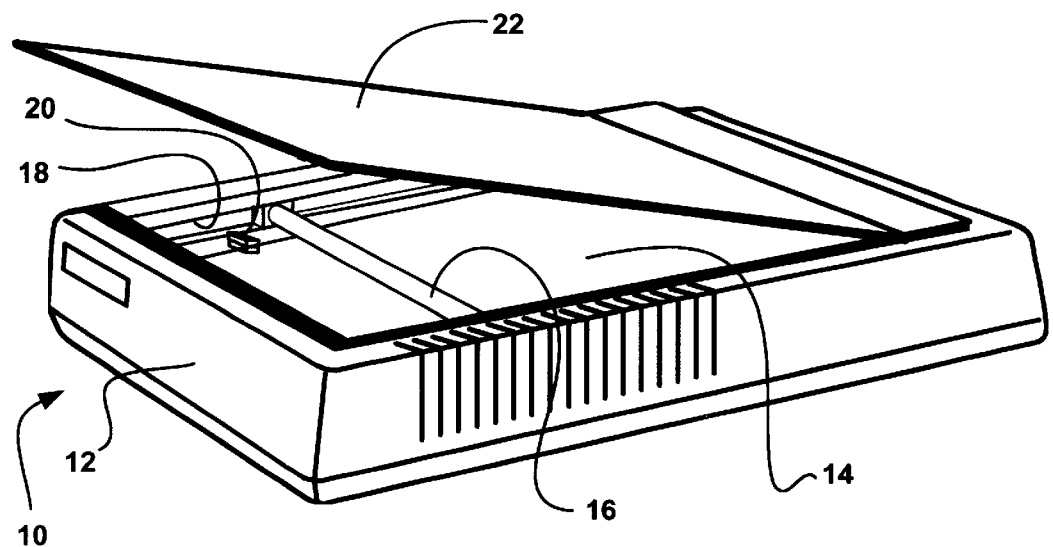
FIG. 1
FIG. 2
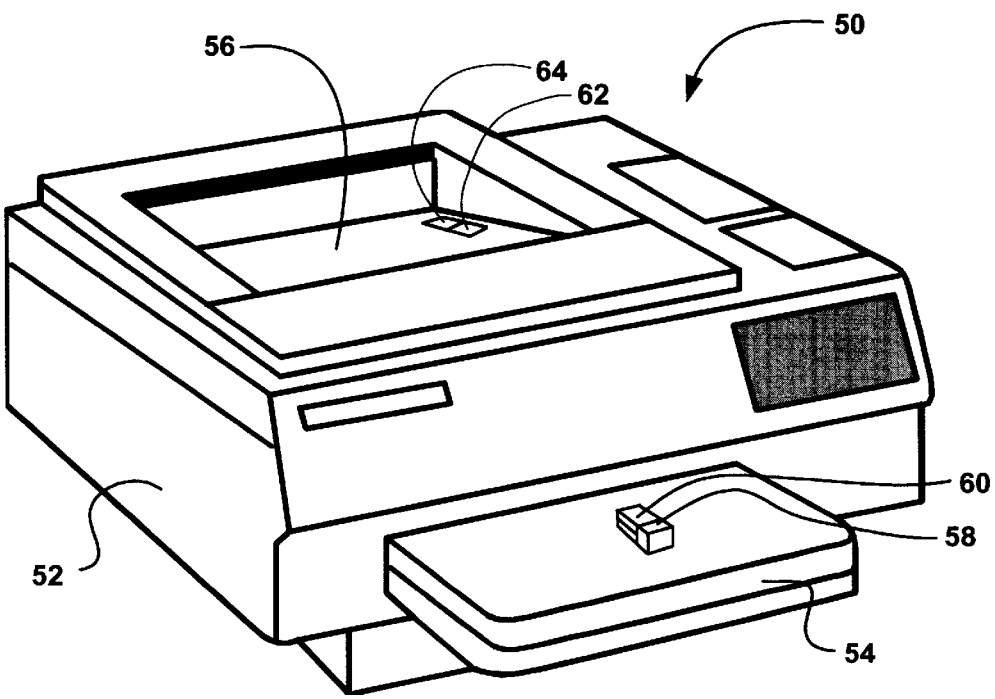

SCANNING AND PRINTING SYSTEMS WITH COLOR DISCRIMINATION

CROSS-REFERENCE TO RELATED APPLICATIONS

The present application contains subject matter related to a concurrently filed U.S. Patent Applications by Ted J. Cooper entitled "OPTICAL SENSOR FOR ILLUMINATION MIXTURES AND METHOD FOR THE DESIGN THEREOF". The related application is assigned to the same assignees as the present application, is identified by U.S. Ser. No. 09/290,357, and is hereby incorporated by reference.

The present application also contains subject matter related to concurrently filed U.S. Patent Applications by Theodore Cooper entitled "ILLUMINATION DETECTING CAMERA", and "COLOR CORRECTING AND AMBIENT LIGHT RESPONSIVE CRT SYSTEM". The related applications are also assigned to the same assignees as the present application and are identified by U.S. Ser. No. 09/290,507 and U.S. Ser. No. 09/209,461, respectively.

TECHNICAL FIELD

The present invention relates generally to document processing equipment and more particularly to monitoring color images and paper color in documents.

BACKGROUND ART

The human vision system is a very poorly understood mechanism that translates photons of various wavelengths into visual pictures that human brains can understand and respond to. The human vision system is extremely sensitive to differences in color.

When a color scanner or printer produces a color reproduction of an original image, even slight color variations produce images which do not look like they have the colors of the original image. The color variations could be in the paper (such as due to aging), the scanner light source, or the printer color toners or ink. For example, in scanners, the light source is generally a long cylindrical fluorescent bulb which is subject to a number of problems. When the light source is first turned on, the color balance of the light varies dynamically along the length of the bulb until the overall temperature stabilizes. During a long sequence of scans, the temperature of the bulb can change sufficiently to shift the color balance causing a color shift in the scanned images over time. Due to the need to frequently turn the light source on and off, each scan produces a slightly different color copy. Little research has been done into how to correct for the apparent visual color differences.

However, extensive research has been undertaken to predict a mathematical construct for visual images, such as photographs, called the White Point (WP). The WP is the illumination that occurred at the brightest point in the picture and represents what should be considered "white" in the final picture. It is assumed that every picture has some white objects or highlights in it. When the brightest object, with roughly equal amounts of red, green, and blue is found, the WP operation is constructed by determining the multipliers of the red, green, and blue parts of the brightest point so that the resulting red, green, and blue values will be made equal. Once this transformation is known for the brightest point in a picture, it is simultaneously applied to all the other points (which are called "dots") in the picture. The WP operation typically results in a final picture that looks much more realistic with respect to its original color balance.

There is a significant shortcoming of the simplistic WP operation described above. It is the assumption that there are some spectrally "white" objects in the picture. While this is true for the majority of pictures, there are also numerous cases where a spectrally "white" object is not present, for example, a close-up picture of a red barn with some blue and green metal signs attached to the barn's side. The dominant color would be red, and, in the reproduction process, this might be interpreted as a color cast problem. The brightest part of the picture would be the green signs. If the algorithm attempted to use the green area as the WP, then the resulting duplicate would be made very blue.

A solution is to measure the original image directly. In color photography, a more sophisticated type of "light meter" called a "photo spectroradiometer" is used. A photo spectroradiometer has to measure numerous points across the visual light spectrum and make a graph of the power at each wavelength that it has found. Once this graph is known, then an accurate representation of the original picture can be constructed by using colors duplicating the graph for different color variations in the paper, the scanner light source, or color toners or ink. In the example of the red barn with the blue and green signs, the photo spectroradiometer graph would show the proper proportions of red, blue, and green even on pale blue paper.

The problem is that a spectroradiometer is both big and expensive. A typical unit is 10 by 6 by 4 inches in size and costs between $5000 to $50,000 in 1998 dollars. It also requires a computer to read out its graphical data and apply it to the image in question. What is needed is a scanner or printer has a low-cost, small, portable spectroradiometer to indicate the color corrections necessary to compensate for the various variations inherent in the scanning or printing process.

DISCLOSURE OF THE INVENTION

The present invention provides a document processing system having an optical sensor system for taking an original color image and compensating for process related variations in the scanning or printing process to provide a scanned or printed image having the color appearance of the original image. The document processing system is provided with an optical sensor system responsive to the scanned document intensity spectrum to provide color compensation for different color variations in the paper, the scanner light source, or the printer color toners or ink.

The present invention further provides a document processing system for monitoring reflective surfaces for changes in the light spectrum using optical sensor systems adapted to recognize light intensity for different color lights.

The present invention further provides a scanner having an optical sensor system which can determine if the scanner light has aged or needs compensation.

The present invention further provides a scanner in which the color of the paper can be compensated for in the scanner's processor to produce pictures that would correspond to the original scene prior to the discoloration due to aging of the document.

The present invention further provides a document printer with an optical sensor system which can track the variance in ink density and colorant solids that are deposited on a document.

The present invention further provides a document printer system having an optical sensor system to track the variance in ink density and colorant solids that are being deposited on the document while monitoring the color of the paper stock to compensate for non-white paper printing conditions.

BRIEF DESCRIPTION OF THE DRAWINGS

FIG. 1 is a scanner according to the present invention;

FIG. 2 is a printer according to the present invention;

BEST MODE FOR CARRYING OUT THE INVENTION

Figure 3:
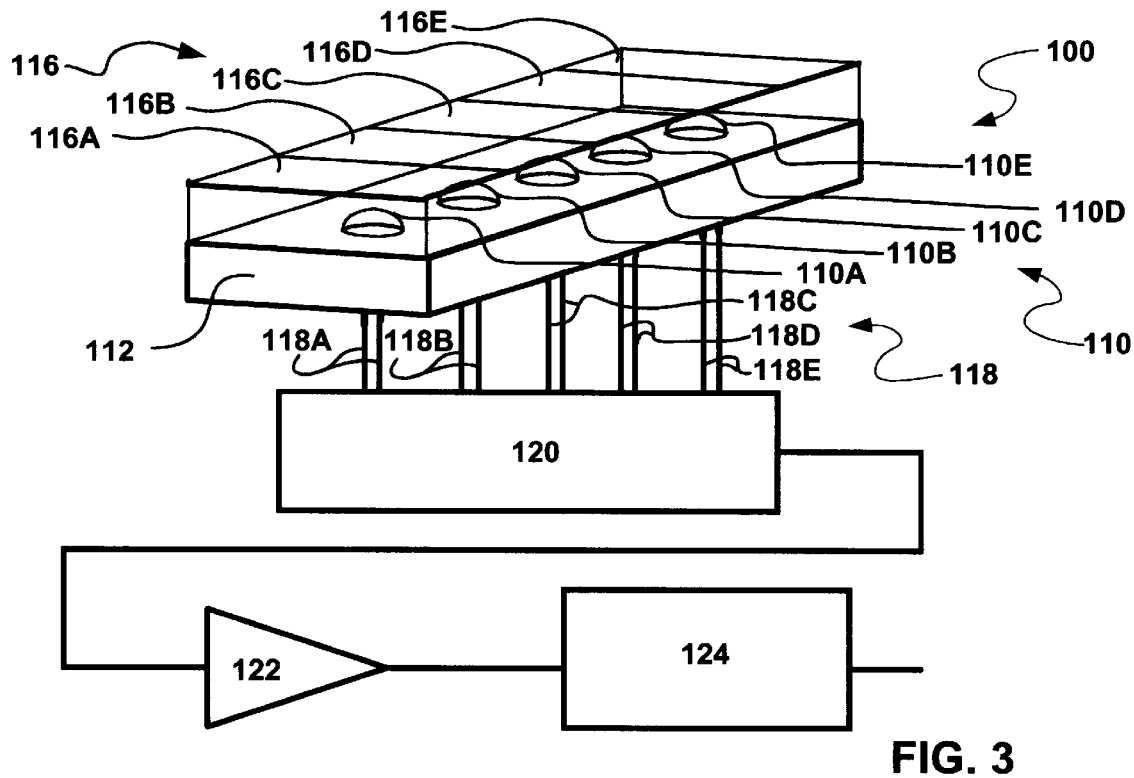
FIG. 3 is an isometric illustration of the bandpass filter optical sensor system used in the present invention.

Referring now to FIG. 1, therein is shown an illustration of a color or black-and-white scanner 10. The scanner 10 is a category of device such as a copier, which is used for converting text and graphic images on a document into electronic form for copying, storage, or further processing. The scanner 10 consists of a body 12 containing a glass plate 14 upon which documents are placed for scanning. A scanner bulb 16 moves in a longitudinal track 18 to illuminate the image on a document. A photosensor 20 is disposed inside the body 12 so as to capture light reflected from the scanner bulb 12 off the document. A cover 22 having a white bottom surface is provided so transparencies and slides can also be scanned. A processor (not shown) controls the scanner 10.

Referring now to FIG. 2, therein is shown a color or black-and-white printer 50. While a desktop model is shown, it should be understood that the present invention is applicable to even larger printing presses. The printer 50 has a body 52 with a paper tray 54 for containing papers to be printed. A conventional mechanism in the body 52 prints the papers and provides them to an output tray 56. A processor (not shown) controls the printer 50.

On top of the paper tray, on the same side as the paper will be printed is a wheat bulb 58 for illuminating the paper and having the light reflected off the paper to a photosensor 60.

In an alternate embodiment, a wheat bulb 62 is positioned next to a photosensor 64 in the bottom of the output tray 56 so as to shine light onto the printed surface of the paper and into the photosensor 64.

Referring now to FIG. 3, therein is shown an optical sensor system 100. The optical sensor system 100 contains four to ten photodiodes 110. The photodiodes 110 are secured to a mounting block 112 which is covered by a clear, optically transparent resin 114. The resin 114 is provided with a flat surface on which a plurality of bandpass filters 116 are disposed. The bandpass filters 116 form a spectrum separation structure for the photodiodes 110.

In the preferred embodiment, the bandpass filters 116 are dyes which are in the form of an ink, paint or gel which can be printed, painted, or silk-screened on the resin 114. The dye material can further be placed in several layers for increased optical density. The different bandpass filters 116 allow the combination to be able to discriminate between different portions of the spectrum of light falling on the bandpass filters 116. With the proper selection of bandpass filters, it is possible to distinguish the particular portions of the spectrum which contain particular intensities which are characteristic of various types of natural and artificial light.

The particular bandpass filter dyes selected and the number of photodiodes in the plurality of photodiodes is determined so as to integrate the signals that are derived from the four to ten photodiodes 110 with their respective bandpass filters 116 in response to various mixtures of illumination. In the present invention five photodiodes 110 A through E are shown with their accompanying bandpass filters 116 A through E. As more tailored bandpass filters that are low cost and easily applied to photodiodes become commercially available, the number of photodiodes and bandpass filters will be adjusted to yield the maximal discrimination and sensitivity to mixed illuminant lighting conditions.

The outputs from the photodiodes 110 are connected by a plurality of leads 118 to a multiplexer or sample-and-hold (S/H) circuitry 120. The analog signals from the (S/H) circuitry 120 are provided to the A/D converter 122. The digital signals are then sent to an application specific integrated circuit (ASIC) 124 which could be a modified version of a conventional integrated circuit which is a part of the equipment, a processor, or an independent ASIC. The ASIC 124 would compare the signals from the photodiodes 110 and provide information as to how the picture taken by the camera 10 should be changed to compensate for differences caused by various mixtures of illuminants. Further, by comparing the strengths of the output signals, a determination can be made of the relative strengths or percentages of the various illuminants. In the preferred embodiment, only the relative strengths of two or possibly three illuminants is necessary to compensate a picture.

Figure 4:
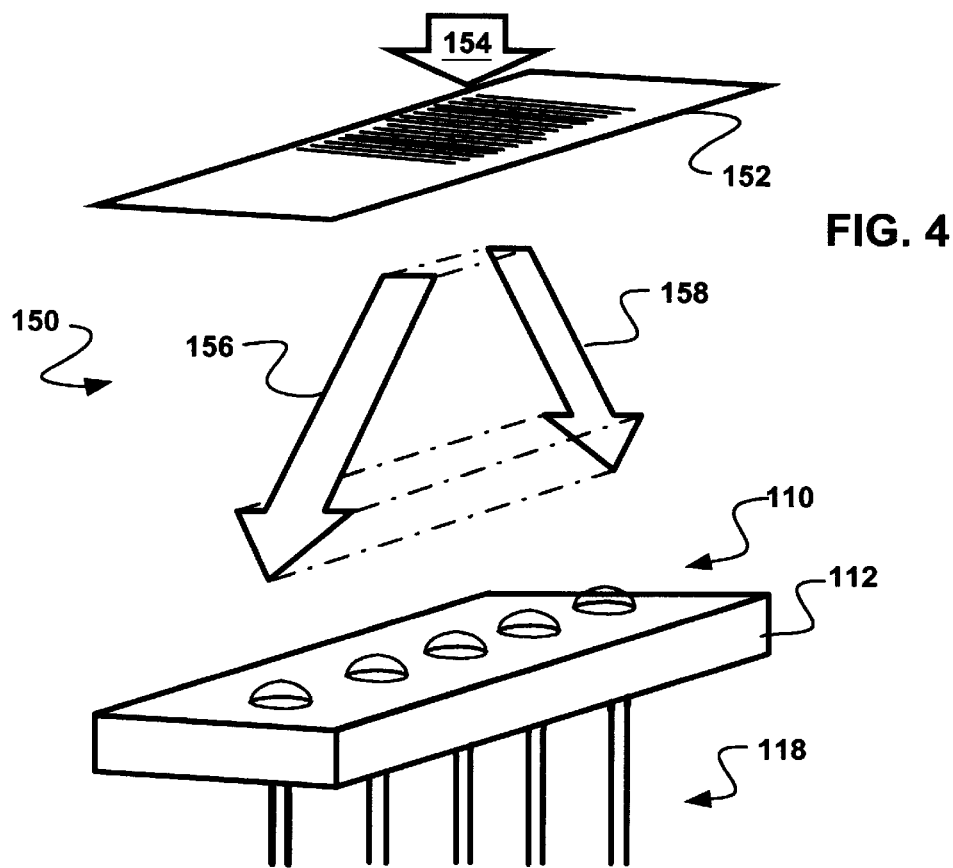
FIG. 4 is an isometric illustration diffraction grating optical sensor system used in the present invention.

Referring now to FIG. 4, therein is shown an alternative optical sensor system 150 having the four to ten photodiodes 110 mounted in a block 112. Spaced away from the block 112 is a diffraction grating 152. The diffraction grating 152 forms a spectrum separation structure for the photodiodes 110.

The diffraction grating 152 diffracts the entering light spectrum 154 containing the light from the various illuminants into its spectral components, represented by spectral components 156 and 158. In this alternate embodiment, for example, the spectral component 156 would be in the red light region and would illuminate the first of the photodiodes 110 while the spectral component 158 would be in blue light region and would illuminate the furthest photodiode 110. Starting with the five pairs of leads 118, the remaining electronics would be the same as for the optical sensor system 100.

In operation, a document is placed picture side down on the glass plate 14 of the scanner 10. The scanner bulb 16 is turned on to move and scan across the face of the image and reflect light into photosensitive elements (not shown) inside the body 12 of the scanner 10. The photosensitive elements provide electronic signals which record:

gray scale for black and white scanners;

red, green, and blue for standard color scanners; and cyan, magenta, yellow, and green for high quality scanners.

In the simplest form, the initial intensity spectrum of the scanner bulb 16 is recorded in the ASIC 124. When the scanner bulb 16 is first turned on, the color balance of the light varies dynamically along the length of the scanner bulb 16 until the overall temperature stabilizes. During a long sequence of scans, the temperature of the scanner bulb 16 can change sufficiently to shift the color balance causing a color shift in the scanned images over time. Due to the need for frequently turning the light source on and off, each scan also produces a slightly different color copy. All these sources of color variation are sensed by the photosensor 20, which could be part of either the optical sensor system 100 or 150. The system 100 or 150 will cause the electronic signals to adjust the color gains to compensate and provide a scanned, compensated image.

In a more complex form, the optical sensor systems 100 and 150 would be able to determine the color of the paper stock used in the scanning and compensate in the recorded image. This permits the proper appearing colors to be printed on different color stock on the printer 50 as will later be described. The various spectrum segments passed by the bandpass filters 116A through E or the diffraction grating 152 will provide different intensities of light at different regions of the spectrum on the photodiodes 110A through E.

The outputs from the photodiodes 110A through E are provided to the S/H 120 which sequentially provides the signals to the A/D converter 122. The A/D converter 122 provides the digital signals to the ASIC 124, the processor, or the ASIC of the scanner 10.

With the diffraction grating optical sensor system 150 as shown in FIG. 4, the diffraction grating 152 breaks up the image and illuminant light, designated as the light 154, into its spectral components 156 and 158 which is spread across the four to ten photodiodes 110. The outputs of the photodiodes 110 then act in the same form as previously described for the bandpass filter optical sensor system 100. While the diffraction grating could be placed on a transparent resin 114, generally the diffraction grating 152 must be spaced away from the block 112, further than the bandpass filters must, in order to cover the spectrum from 400 to 700 nanometers.

In the operation of the color or black-and-white printer 50, the photosensor 60 is placed over the paper tray 54 and a small wheat bulb 58 is used to illuminate the paper. The photosensor 60 using the optical sensor system 100 can detect color or aged paper. It should be noted that by using a wheat bulb 58 which is a light source providing a known spectrum of light, it would be possible for the photosensor 60 to determine the color of the paper independent of any extraneous light source.

In order to determine proper color settings of the printer 50, the paper could be printed with color marks in the margins of the paper which could be read by the photosensor 64 illuminated by a wheat bulb 62. Since the photosensor 64 would be located in the output tray 56 where there is additional room, a diffraction grating optical sensor system 15 could be used to detect the variance in toner or ink density and colorant solids that are deposited on the paper.

While the present invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations which fall within the spirit and scope of the included claims. All matters set forth herein or shown in the accompanying drawings are to be interpreted in an illustrative and non-limiting sense.

The invention claimed is:

1. Document processing equipment having an optical sensor system comprising:

four to ten photosensors for providing a plurality of outputs proportional to the light energy applied thereto;

a spectrum separation structure for said four to ten photosensors, said spectrum separation structure having discrimination ability for portions of the spectrum of light selected from a group consisting of red, green, blue, cyan, magenta, yellow, gray scale, and a combination thereof; and a processing system connected to said four to ten photosensors and responsive to said plurality of outputs to determine the presence of light energy attributable to red, green, blue, cyan, magenta, yellow, and gray scale light and the combinations thereof.

2. The sensor system as claimed in claim 1 wherein:

said spectrum separation structure includes a diffraction grating for providing a spectrum with light energy distribution to said four to ten photosensors; and said processing system including circuitry responsive to said plurality of outputs to determine the proportions of the red, green, blue, cyan, magenta, and yellow light and the combinations thereof.

3. The sensor system as claimed in claim 1 wherein:

said spectrum separation structure includes a plurality of bandpass filters, each of said bandpass filter associated with one of said four to ten photosensors and capable of discriminating among the red, green, blue, magenta, cyan, and yellow light and the combinations thereof.

4. The sensor system as claimed in claim 3 including:

said four to ten photosensors sensitive to reflected light off a document and the colored areas thereon and through said plurality of bandpass filters to provide said plurality of outputs.

5. The sensor system as claimed in claim 3 including:

a light source capable of illuminating a document having colored areas thereon; and said photosensors sensitive to reflected light off the document and the colored areas thereon and through said plurality of bandpass filters to provide said plurality of outputs.

6. The sensor system as claimed in claim 5 wherein:

said processing system includes further circuitry for determining the white point of the reflected light and providing information for adjusting said plurality of outputs to compensate therefor.

7. A scanner having a reflective surface optical sensor comprising:

four to ten photosensors for providing a plurality of outputs proportional to the light energy applied thereto;

a spectrum separation structure for said four to ten photosensors, said spectrum separation structure having discrimination ability for portions of the spectrum of light selected from a group consisting of red, green, blue, cyan, magenta, yellow, and a combination thereof; and a processing system connected to said four to ten photosensors and responsive to said plurality of outputs to determine the presence of light energy attributable to red, green, blue, cyan, magenta, and yellow light and the combinations thereof, said processing system including a mechanism for providing information to allow compensation for changes in the light over time.

8. The scanner as claimed in claim 7 wherein:

said spectrum separation structure includes a diffraction grating for providing a spectrum with light energy distribution to said four to ten photosensors; and said processing system including circuitry responsive to said plurality of outputs to determine the proportions of the red, green, blue, cyan, magenta, and yellow light and the combinations thereof.

9. The scanner as claimed in claim 7 wherein:

said spectrum separation structure includes a plurality of bandpass filters, each of said bandpass filter associated with one of said four to ten photosensors and capable of discriminating among the red, green, blue, magenta, cyan, and yellow light and the combinations thereof.

10. The scanner as claimed in claim 9 including:

said four to ten photosensors sensitive to reflected light off a document and the colored areas thereon and through said plurality of bandpass filters to provide said plurality of outputs.

11. The scanner as claimed in claim 9 including:

a light source capable of illuminating a document having colored areas thereon; and said photosensors sensitive to reflected light off the document and the colored areas thereon and through said plurality of bandpass filters to provide said plurality of outputs.

12. The scanner as claimed in claim 9 wherein:

said processing system includes further circuitry for determining the white point of the reflected light and providing information for adjusting said plurality of outputs to compensate therefor.

13. A color printer having a reflective surface optical sensor comprising:

four to ten photosensors for providing a plurality of outputs proportional to the light energy applied thereto;

a spectrum separation structure for said four to ten photosensors, said spectrum separation structure having discrimination ability for portions of the spectrum of light selected from a group consisting of red, green, blue, cyan, magenta, yellow, and a combination thereof; and a processing system connected to said four to ten photosensors and responsive to said plurality of outputs to determine the presence of light energy attributable to red, green, blue, cyan, magenta, and yellow light and the combinations thereof, said processing system including a mechanism for providing information to allow compensation for changes in the light over time.

14. The printer as claimed in claim 13 wherein:

said spectrum separation structure includes a diffraction grating for providing a spectrum with light energy distribution to said four to ten photosensors; and said processing system including circuitry responsive to said plurality of outputs to determine the proportions of the red, green, blue, cyan, magenta, and yellow light and the combinations thereof.

15. The printer as claimed in claim 13 wherein:

said spectrum separation structure includes a plurality of bandpass filters, each of said bandpass filter associated with one of said four to ten photosensors and capable of discriminating among the red, green, blue, magenta, cyan, and yellow light and the combinations thereof.

16. The printer as claimed in claim 13 including:

said four to ten photosensors sensitive to reflected light off a document and the colored areas thereon and through said plurality of bandpass filters to provide said plurality of outputs.

17. The printer as claimed in claim 13 including:

a light source capable of illuminating a document having colored areas thereon; and said photosensors sensitive to reflected light off the document and the colored areas thereon and through said plurality of bandpass filters to provide said plurality of outputs.

18. The printer as claimed in claim 13 wherein:

said processing system includes further circuitry for determining the white point of the reflected light and providing information for adjusting said plurality of outputs to compensate therefor.

\* \* \* \* \*